United States Patent [19]
Brown et al.

[11] Patent Number: 5,965,745
[45] Date of Patent: Oct. 12, 1999

[54] INDOLE CARBAMATES AS LEUKOTRIENE ANTAGONISTS

[75] Inventors: Matthew F. Brown, Pawcatuck; Anthony Marfat, Mystic, both of Conn.

[73] Assignee: Pfizer Inc, New York, N.Y.

[21] Appl. No.: 09/051,364

[22] PCT Filed: Aug. 26, 1996

[86] PCT No.: PCT/IB96/00832

§ 371 Date: Jul. 1, 1998

§ 102(e) Date: Jul. 1, 1998

[87] PCT Pub. No.: WO97/13751

PCT Pub. Date: Apr. 17, 1997

Related U.S. Application Data

[60] Provisional application No. 60/005,003, Oct. 10, 1995.

[51] Int. Cl.⁶ .................. C07D 209/10; C07D 403/06; C07D 401/06; C07D 413/06; A61R 31/40
[52] U.S. Cl. .................. 548/479; 514/235.2; 514/253; 514/323; 514/339; 514/414; 514/415; 544/153; 544/373; 546/208; 546/278.4; 548/500; 548/506; 548/510; 548/454
[58] Field of Search .................. 548/510, 506, 548/500, 479, 454; 514/414, 415, 235.2, 253, 323, 339; 544/153, 373; 546/208, 278.4

[56] References Cited

U.S. PATENT DOCUMENTS 5,280,039 1/1994 Eggler ........................ 514/414
5,399,714 3/1995 Gerspacher et al. ........... 548/510

FOREIGN PATENT DOCUMENTS 0646587 3/1993 Australia ........................ 548/510

OTHER PUBLICATIONS

Brown et al, J. Med. Chem., vol. 35(13), pp. 2419 to 2439, 1992.

Jacobs et al, J. Med. Chem., vol. 37(9), pp. 1282 to 1297, 1994.

*Primary Examiner*—Floyd D. Higel
*Attorney, Agent, or Firm*—Peter C. Richardson; Paul H. Ginsburg; Jacob M. Levine

[57] ABSTRACT

Compounds of the formula

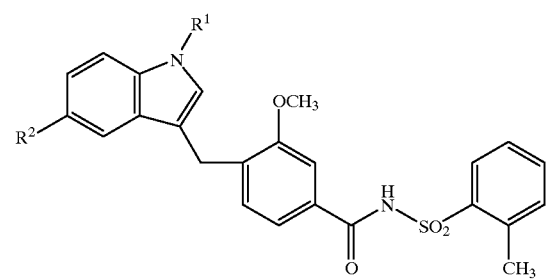

wherein $R^1$ AND $R^2$ are as defined, useful in the treatment of asthma, rheumatoid arthritis, osteoarthritis, bronchitis, chronic obstructive airways diseases, psoriasis, allergic rhinitis, atopic dermatitis, shock, and other inflammatory diseases and for blocking the leucotriene D4 receptor, pharmaceutical compositions containing such compounds and methods of blocking leucotriene D4 receptors using such compositions.

11 Claims, No Drawings

INDOLE CARBAMATES AS LEUKOTRIENE ANTAGONISTS

This application claims the benefit of Provisional application Ser. No. 60/005,003 filed Oct. 10, 1995.

This application is a Section 371 National Stage filing of PCT/IB 96/00832, filed Aug. 26, 1996.

BACKGROUND OF THE INVENTION

The present invention relates to N-o-tolylsulfonylbenzamide compounds, pharmaceutical compositions comprising such compounds and the use of such compounds as antagonists of leukotriene D4. The compounds of this invention are useful in the treatment of inflammatory diseases.

It is known that arachidonic acid (AA) is metabolized in mammals by two distinct pathways. The metabolism of arachidonic acid by cyclooxygenase enzymes results in the production of prostaglandins and thromboxanes. The other pathway of AA metabolism involves lipoxygenase enzymes and results in the production of a number of oxidative products called leukotrienes. The latter are designated by the LT nomenclature system, and one of the most significant products of the lipoxygenase metabolic pathway is the leukotriene D4. Leukotrienes participate in inflammatory reactions, exhibit chemotactic activities, stimulate lysosomal enzyme release and act as important factors in the immediate hypersensitivity reaction. For example, LTD4 is a potent bronchoconstrictor of the human bronchi.

The biological activity of the leukotrienes indicates that a rational approach to drug therapy to prevent, remove or ameliorate the symptoms of asthma, rheumatoid arthritis, osteoarthritis, bronchitis, chronic obstructive airways disease, psoriasis, allergic rhinitis, atopic dermatitis, shock and other inflammatory diseases must focus on either blocking the release of mediators of these conditions or antagonizing their effects. Thus, compounds which inhibit the biological effects of the leukotrienes are considered to be of value in treating such conditions defined above.

SUMMARY OF THE INVENTION

The present invention relates to a compound of the formula

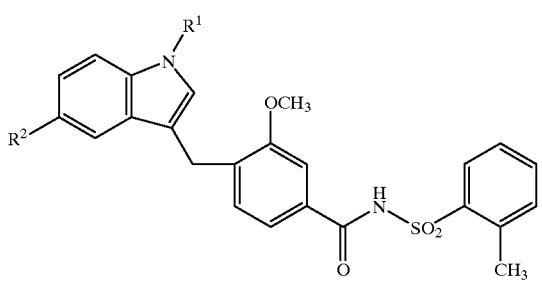

I or a pharmaceutically acceptable salt thereof, wherein $R^1$ is CHO, $CH_2F$, $CHF_2$ or $CONR^3R^4$ wherein $R^3$ and $R^4$ are each independently selected from the group consisting of hydrogen, $(C_1-C_6)$alkyl, $(C_2-C_5)$alkenyl, $(C_2-C_6)$alkynyl, $(C_6-C_{10})$aryl, $(C_6-C_{10})$aryl$(C_1-C_6)$alkyl, $((C_1-C_6)$alkyl)$_2$amino$(C_1-C_5)$alkyl, pyridinyl and $CHR^5R^6$ wherein $R^5$ and $R^6$ are each independently $(C_1-C_6)$alkyl or $(C_8-C_{10})$aryl;

or $R^3$ or $R^4$ may be taken together with the nitrogen to which they are attached to form morpholinyl, pyrrolidinyl or a group of the formula

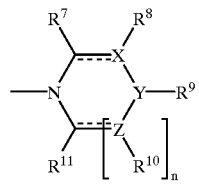

wherein the broken lines represent optional double bonds;
n is 0, 1 or 2;
X, Y and Z are each independently CH, O, S or N; and
$R^7R^8$, $R^9$, $R^{10}$ and $R^{11}$ are each independently selected from the group consisting or hydrogen, $(C_1-C_6)$alkyl, $(C_2-C_6)$alkenyl, $(C_2-C_6)$alkynyl, $(C_8-C_{10})$aryl, $(C_6-C_{10})$aryl$(C_1-C_6)$alkyl, $((C_1-C_6)$alkyl)$_2$amino$(C_1-C_6)$alkyl, pyridinyl, $CHR^5R^6$ wherein $R^5$ and $R^6$ are each independently $(C_1-C_6)$alkyl or $(C_6-C_{10})$aryl; or benzhydryl optionally substituted by one to five halo;

$R^2$ is a group of the formula

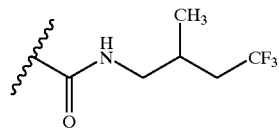

or a group of the formula

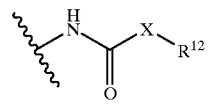

wherein X is O, NH or $CH_2$; and
$R^{12}$ is $(C_3-C_7)$cycloalkyl or a group of the formula

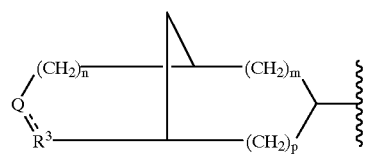

wherein the broken line represents an optional double bond; n is 0 or 1; m is 0, 1 or 2; p is 0, 1 or 2; Q and $R^3$ are both CH or both $CH_2$;

with the proviso that when Q and $R^3$ are both CH, the broken line represents a double bond; and with the proviso that when n is 1 or 2, only two of the three variables X, Y and Z can be O, S or N.

The term "alkyl", as used herein, unless otherwise indicated, includes saturated monovalent hydrocarbon radicals having straight, branched or cyclic moieties or combinations thereof, optionally substituted by 1 to 3 halo.

The term "aryl", as used herein, unless otherwise indicated, includes an organic radical derived from an aromatic hydrocarbon by removal of one hydrogen, such as phenyl or naphthyl, optionally substituted by 1 to 3 substituents selected from the group consisting of fluoro, chloro, trifluoromethyl, $(C_1-C_6)$alkoxy, $(C_6-C_{10})$aryloxy, trifluoromethoxy, difluoromethoxy and $(C_1-C_6)$alkyl.

Preferred compounds of formula I include those wherein $R^1$ is $CONR^3R^4$ wherein $R^3$ and $R^4$ are each independently selected from $(C_1-C_6)$alkyl, $(C_6-C_{10})$aryl and $(C_6-C_{10})$aryl$(C_1-C_6)$alkyl.

Other preferred compounds of formula I include those wherein X is O and $R^{12}$ is cyclopentyl.

Other preferred compounds of formula I include those wherein $R^1$ is $CONR^3R^4$ wherein $R^3$ and $R^4$ are each independently selected from $(C_1-C_6)$alkyl, $(C_6-C_{10})$aryl and $(C_6-C_{10})$aryl$(C_1-C_6)$alkyl; X is $CH_2$ and $R^{12}$ is cyclopentyl.

Specific preferred compounds of formula I include the following:

4-[1-formyl-5-(cyclopentyloxycarbonyl)amino-1H-indol-3-ylmethyl]-3-methoxy-N-o-tolylsulfonylbenzamide;

4-[1-(hydroxycarbamoyl)-5-(cyclopentyloxycarbonyl)amino-1H-indol-3-ylmethyl]-3-methoxy-N-o-tolylsulfonylbenzamide;

4-[1-((2-carboxyethyl)carbamoyl)-5-(cyclopentyloxycarbonyl)amino-1H-indol-3-ylmethyl]-3-methoxy-N-o-tolylsulfonylbenzamide;

4-[1-((2-tetrazolylethyl)carbamoyl)-5-(cyclopentyloxycarbonyl)amino-1H-indol-3-ylmethyl]-3-methoxy-N-o-tolylsulfonylbenzamide;

4-[1-(methylphenylcarbamoyl)-5-(cyclopentyloxycarbonyl)amino-1H-indol-3-ylmethyl]-3-methoxy-N-o-tolylsulfonylbenzamide;

4-[1-(diphenylcarbamoyl)-5-(cyclopentyloxycarbonyl)amino-1H-indol-3-ylmethyl]-3-methoxy-N-o-tolylsulfonylbenzamide;

4-[1-carbamoyl-5-(cyclopentyloxycarbonyl)amino-1H-indol-3-ylmethyl]-3-methoxy-N-o-tolylsulfonylbenzamide; and 4-[1-(pyrrolidine-carbonyl)-5-(cyclopentyloxycarbonyl)amino-1H-indol-3-ylmethyl]-3-methoxy-N-o-tolylsulfonylbenzamide.

The present invention also relates to a pharmaceutical composition for (a) treating a condition selected from the group consisting of asthma, rheumatoid arthritis, osteoarthritis, bronchitis, chronic obstructive airways disease, psoriasis, allergic rhinitis, atopic dermatitis, shock, and other inflammatory diseases or (b) blocking the leukotriene D4 receptor in a mammal, including a human, comprising a leukotriene D4 receptor blocking amount of a compound according to formula I and a pharmaceutically acceptable carrier.

The present invention also relates to a method of treating a condition selected from the group consisting of asthma, rheumatoid arthritis, osteoarthritis, bronchitis, chronic obstructive airways disease, psoriasis, allergic rhinitis, atopic dermatitis, shock, and other inflammatory diseases in a mammal, including a human, comprising administering to said mammal an amount of a compound according to formula I effective in treating such a condition.

The present invention also relates to a method of blocking the leukotriene D4 receptor in a mammal, including a human, comprising administering to said mammal a leukotriene D4 receptor blocking amount of a compound according to formula I.

DETAILED DESCRIPTION OF THE INVENTION

The following reaction scheme illustrates the preparation of the compounds of the present invention. Unless otherwise indicated $R^3$, $R^4$ and $R^{12}$ in the reaction Schemes and the discussion that follow are defined as above.

Scheme 1

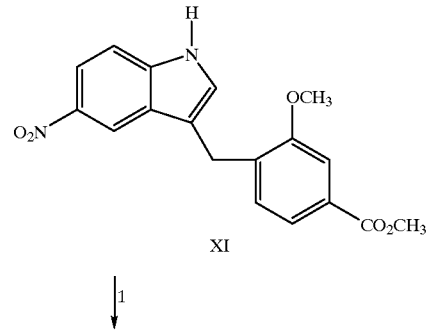

XI

↓1

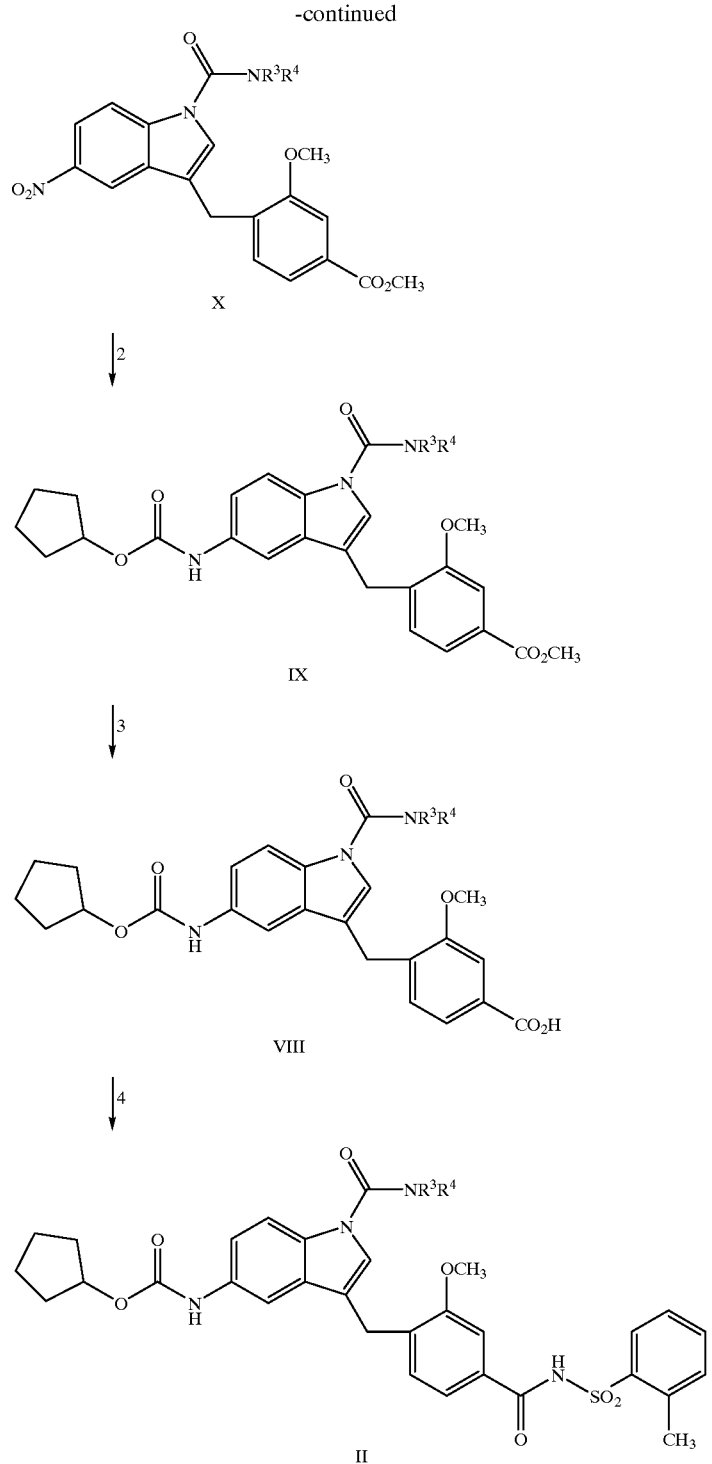

Scheme 2
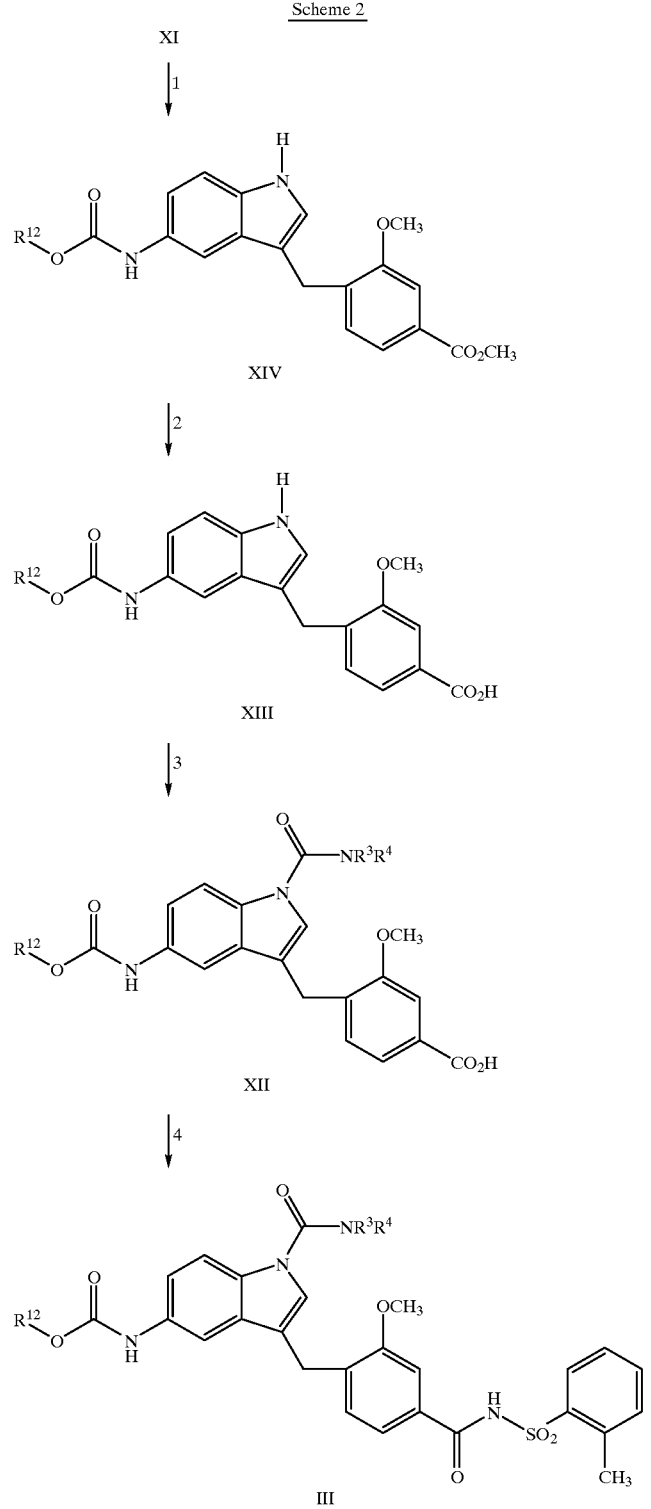

Scheme 3
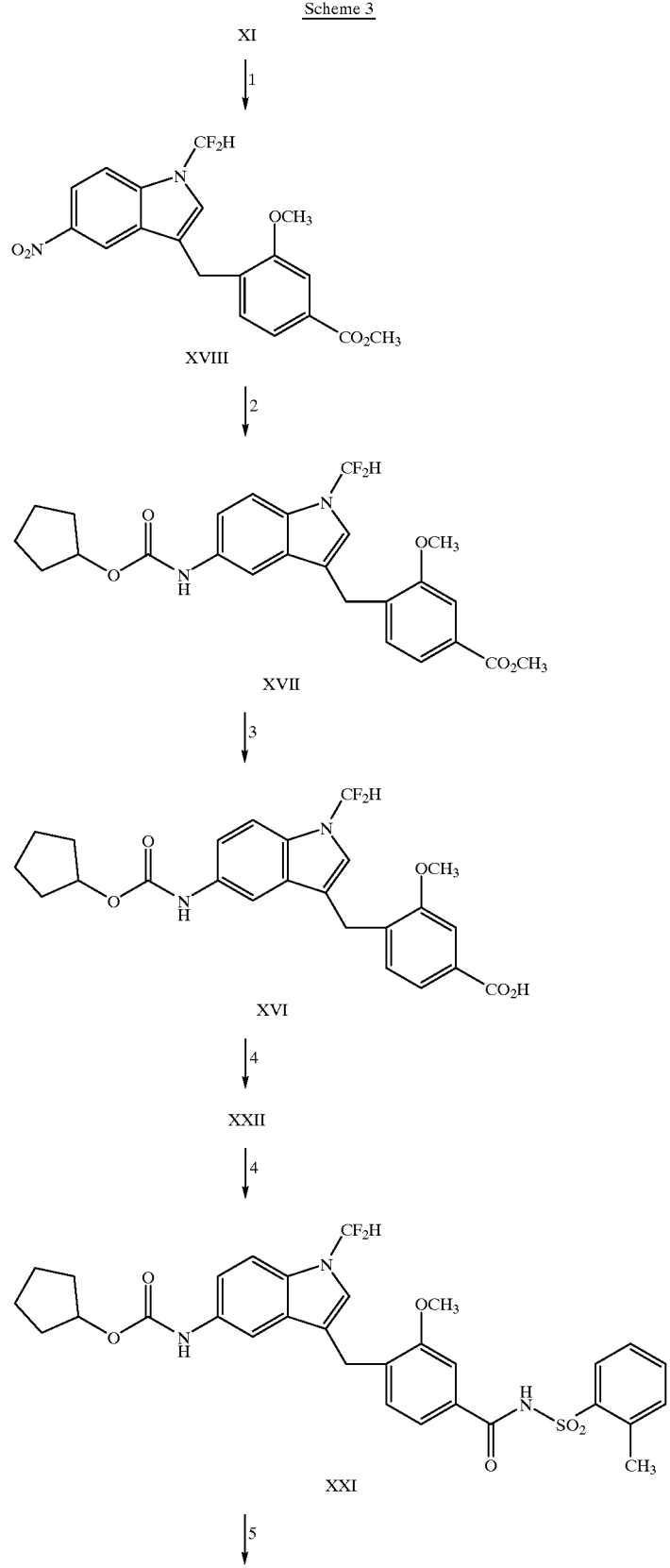

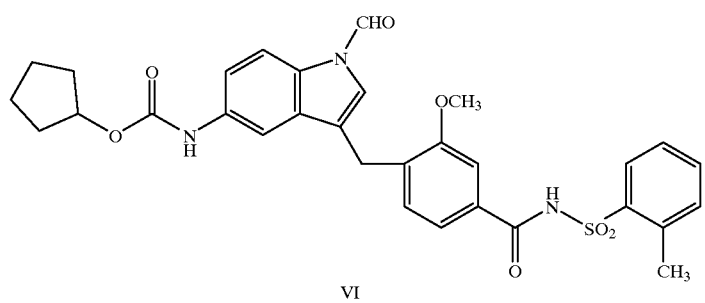
VI
Scheme 4
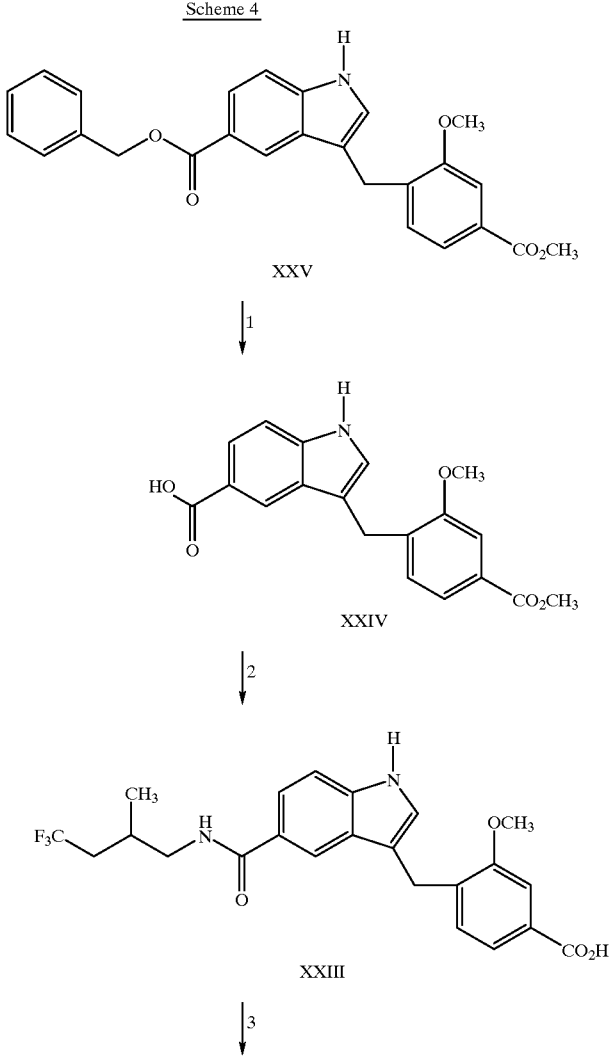

-continued
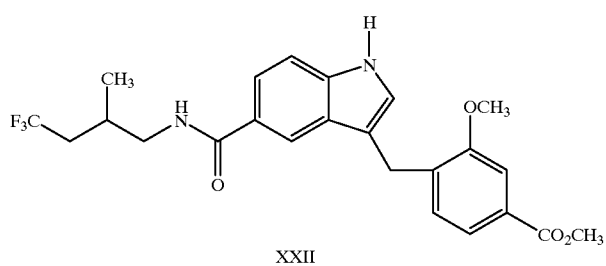
XXII
↓ 4
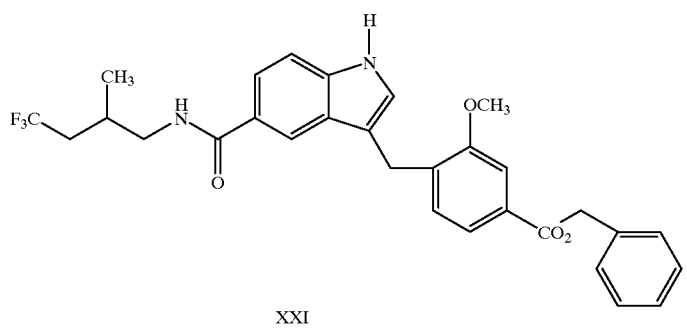
XXI
↓ 5
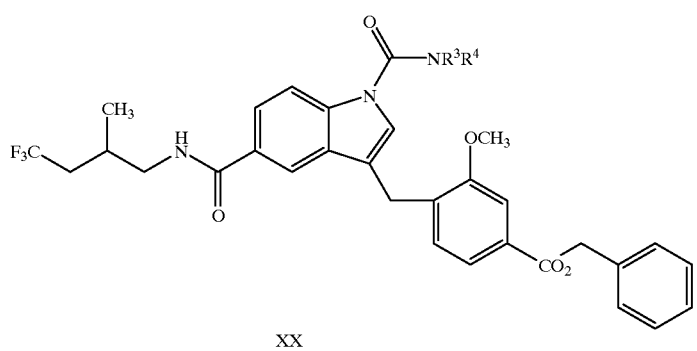
XX
↓ 6
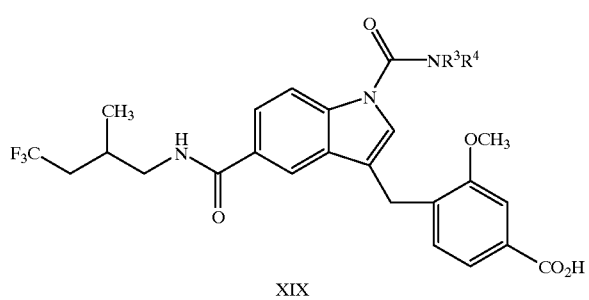
XIX
↓ 7

-continued

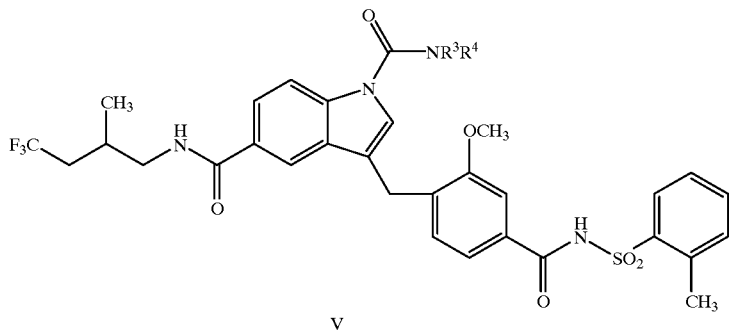

V

In reaction 1 of Scheme 1, the compound of formula XI is converted to the corresponding 4-[1-($R^3R^4$carbamoyl)-1H-indol-3-ylmethyl]-benzoic acid methylester compound of formula X, wherein $R^3$ and $R^4$ are as defined above, by reacting a solution of XI and triethylamine in a polar aprotic solvent, such as methylene chloride, at a temperature between about −10° C. to about 0° C., preferably about 0° C., with a solution of phosgene in an aprotic solvent, such as toluene. The reaction mixture is warmed to room temperature and allowed to stir for a time period between about 30 minutes to about 1.5 hours, preferably about 1 hour. To the reaction mixture so formed is added a compound of the formula NH$R^3R^4$, wherein $R^3$ and $R^4$ are as defined above, and the resulting reaction mixture is stirred for an additional time period between about 10 hours to about 14 hours, preferably about 12 hours.

The compound of formula XI is converted to the corresponding 4-[1-($R^3R^4$carbamoyl)-1H-indol-3-ylmethyl]-benzoic acid methylester compound of formula X, wherein $R^3$ is as defined above and $R^4$ is hydrogen, by reacting a solution of XI and 4-dimethylaminopyridine in a polar aprotic solvent, such as methylene chloride, with a compound of the formula $R^3$NCO, wherein $R^3$ is as defined above. The resulting reaction mixture is stirred at room temperature for a time period between about 16 hours to about 20 hours, preferably about 18 hours.

The compound of formula XI is converted to the corresponding 4-[(1-$R^3R^4$carbamoyl)-1H-indol-3-ylmethyl]-benzoic acid compound of formula X, wherein $R^3$ and $R^4$ are both hydrogen, by reacting XI with chlorosulfonylisocyanate in a polar aprotic solvent, such as methylene chloride. The reaction mixture is stirred at room temperature for a time period between about 4 days to about 6 days, preferably about 5 days.

In reaction 2 of Scheme 1, the 4-[5-nitro-1H-indol-3-ylmethyl] benzoic acid methylester compound of formula X is converted to the corresponding 4-[5-(cyclopentyloxycarbonyl)amino-1H-indol-3-ylmethyl]-benzoic acid methylester compound of formula IX by hydrogenating X in the presence of a catalyst, such as 10% palladium on carbon, and a 1:1 ratio mixture of tetrahydrofuran and methanol. To a solution of the corresponding amine so formed and N-methylmorpholine in a polar aprotic solvent, such as methylene chloride, is added cyclopentylchloroformate. The resulting reaction mixture is stirred at room temperature for a time period between about 10 minutes to about 20 minutes, preferably about 15 minutes, and treated with an acid, preferably hydrochloric acid.

In reaction 3 of Scheme 1, the benzoic acid methylester compound of formula IX is converted to the corresponding benzoic acid compound of formula VIII by (a) heating IX with lithium iodide in the presence of pyridine to reflux for a time period between about 10 hours to about 14 hours, preferably about 12 hours, or (b) treating IX with lithium hydroxide monohydrate in the presence of a 2:2:1 ratio mixture of tetrahydrofuran, methanol and water.

The benzoic acid methylester of formula IX is converted to the corresponding benzoic acid compound of formula VIII, wherein $R^3$ is as defined above and $R^4$ is hydrogen or $R^3$ and $R^4$ are both hydrogen, by treating IX with lithium hydroxide monohydrate in the presence of a 2:2:1 ratio mixture of tetrahydrofuran, methanol and water. The reaction mixture is stirred at room temperature for a time period between about 10 hours to about 14 hours, preferably about 12 hours.

In reaction 4 of Scheme 1, the benzoic acid compound of formula VIII is converted to the corresponding N-o-tolylsulfonylbenzamide compound of formula II by reacting a solution of VIII, 4-dimethylaminopyridine and 1-[3-dimethylamino)propyl]-3-ethylcarbodiimide hydrochloride in a polar aprotic solvent, such methylene chloride, with o-tolylsulfonamide. The resulting reaction mixture is stirred for a time period between about 10 hours to about 14 hours, preferably about 12 hours, at room temperature.

In reaction 1 of Scheme 2, the compound of formula XI is converted to the corresponding 4-[5-($R^{12}$oxycarbonyl)amino]-1H-indol-3-ylmethyl]-benzoic acid methylester of formula XIV by reacting XI with tin (II) chloride dihydrate in a polar protic solvent, such as ethanol. The reaction mixture is heated to reflux for a time period between about 20 hours to about 28 hours, preferably about 24 hours. To a solution of the corresponding amine so formed and N-methylmorpholine in a polar aprotic solvent, such as methylene chloride, is added a compound of the formula $R^{12}$OCOCl, wherein $R^{12}$ is as defined above. The resulting reaction mixture is stirred for a time period between about 30 minutes to about 1.5 hours, preferably about 1 hour, at room temperature.

In reaction 2 of Scheme 2, the benzoic acid methylester of formula XIV is converted to the corresponding benzoic acid compound of formula XIII by treating XIV with lithium hydroxide monohydrate in the presence of a 2:2:1 ratio mixture of tetrahydrofuran, methanol and water. The reaction mixture is stirred at room temperature for a time period between about 10 hours to about 14 hours, preferably about 12 hours.

In reaction 3 of Scheme 2, the benzoic acid compound of formula XIII is converted to the corresponding 4-[1-($R^3R^4$carbamoyl)-1H-indol-3-ylmethyl]-benzoic acid compound of formula XII by reacting a solution of XIII in a polar aprotic solvent, such as dimethylformamide, with a solution of sodium hydride in a polar aprotic solvent, such as dimethylformamide, at a temperature between about −10° C. to about 10° C., preferably about 0° C. After stirring the reaction mixture for a time period between about 10 minutes to about 30 minutes, preferably about 20 minutes, a compound of the formula $R^3R^4$NCOCl, wherein $R^3$ and $R^4$ are as defined, is added and the resulting reaction mixture is allowed to stir for an additional time period between about 30 minutes to about 1.5 hours, preferably about 1 hour.

In reaction 4 of Scheme 2, the benzoic acid compound of formula XII is converted to the corresponding N-o-tolylsulfonylbenzamide compound of formula III according to the procedure described above in reaction 4 of Scheme 1.

In reaction 1 of Scheme 3, the compound of formula XI is converted to the corresponding 4-(1-difluoromethyl-1H-indol-3-ylmethyl)-benzoic acid methylester compound of formula XVII by treating XI with sodium hydride in a polar aprotic solvent, such as dimethylformamide. The reaction mixture is stirred at room temperature for a time period between about 10 minutes to about 30 minutes, preferably about 20 minutes. Freon is then bubbled into the reaction mixture for a time period between about 3 minutes to about 7 minutes, preferably about 5 minutes, and the resulting reaction mixture is quenched with water.

In reaction 2 of Scheme 3, the 4-[5-nitro-1H-indol-3-ylmethyl]-benzoic acid methylester compound of formula XVIII is converted to the corresponding 4-[5-(cyclopentyloxycarbonyl)amino-1H-indol-3-ylmethyl]-benzoic acid methylester compound of formula XVII according to the procedure described above in reaction 2 of Scheme 1.

In reaction 3 of Scheme 3, the benzoic acid methylester compound of formula XVII is converted to the corresponding benzoic acid compound of formula XVI according to the procedure described above in reaction 2 of Scheme 2.

In reaction 4 of Scheme 3, the benzoic acid compound of formula XVI is converted to the corresponding N-o-tolylsulfonylbenzamide compound of formula XV according to the procedure described above in reaction 4 of Scheme 1.

In reaction 5 of Scheme 3, the 4-(1-difluoromethyl-1H-indol-3-ylmethyl)-N-o-tolylsulfonylbenzamide compound of formula XV is converted to the corresponding 4-(1-formyl-1H-indol-3-ylmethyl)-N-o-tolylsulfonylbenzamide compound of formula IV by treating a solution of VI in a polar aprotic solvent, such as chloroform, with a solution of hydrochloric acid in ether. The resulting reaction mixture is stirred at room temperature for a time period between about 3 hours to about 5 hours, preferably about 4 hours.

In reaction 1 of Scheme 4, the compound of formula XXV is converted to the corresponding carboxylic acid compound of formula XXIV by hydrogenating XXV in the presence of a catalyst, such as 10% palladium on carbon, formic acid and a polar aprotic solvent, such as dimethylformamide.

In reaction 2 of Scheme 4, the carboxylic acid compound of formula XXIV is converted to the corresponding 4-[5-(4,4,4-trifluoro-2-methyl-butylcarbamoyl)-1H-indol-3-ylmethyl]-benzoic acid methylester compound of formula XXIII by reacting XXIV with 4-dimethylaminopyridine, 1-(3-dimethylaminopropyl)-3-ethylcarbodiimide hydrochloride, triethylamine and 4,4,4-trifluoro-2-methylbutylamine hydrochloride in a polar aprotic solvent, such as methylene chloride. The reaction mixture was stirred at room temperature for a time period between about 10 hours to about 14 hours, preferably about 12 hours.

In reaction 3 of Scheme 4, the benzoic acid methylester compound of formula XXIII is converted to the corresponding benzoic acid compound of formula XXII according to the procedure described above in reaction 2 of Scheme 2.

In reaction 4 of Scheme 4, the benzoic acid compound of formula XXII is converted to the corresponding benzoic acid benzylester compound of formula XXI by reacting a solution of XXII, triphenylphospine and benzyl alcohol in an aprotic solvent, such as tetrahydrofuran, with diethyl azodicarboxylate at a temperature between about −10° C. to about 10° C., preferably about 0° C. The reaction mixture is warmed to room temperature and stirred for a time period between about 10 hours to about 14 hours, preferably about 12 hours.

In reaction 5 of Scheme 4, the benzoic acid benzylester compound of formula XXI is converted to the corresponding 4-[1-($R^3R^4$carbamoyl)-1H-indol-3-ylmethyl]-benzoic acid benzylester compound of formula XX according to the procedure described above in reaction 3 of Scheme 2.

In reaction 6 of Scheme 4, the benzoic acid benzylester compound of formula XX is converted to the corresponding benzoic acid compound of formula XIX by hydrogenating XX in the presence of a catalyst, such as 10% palladium on carbon and a mixture of tetrahydrofuran ethyl acetate.

In reaction 7 of Scheme 4, the benzoic acid compound of formula XIX is converted to the corresponding N-o-tolylsulfonylbenzamide compound of formula V according to the procedure described above in reaction 4 of Scheme 1.

The compounds of the formula I and their pharmaceutically acceptable salts (the compounds of the present invention) are useful as selective antagonists of leukotriene D4, i.e., they possess the ability to block the leukotriene D4 receptor in mammals, and therefore they are able to function as therapeutic agents in the treatment of the aforementioned disorders and diseases in an afflicted mammal.

The compounds of the present invention are believed to be antagonists of leukotriene D4 and therefore are of value in the treatment of a wide variety of clinical conditions the treatment of which are effected or facilitated by blocking the leukotriene D4 receptor. Such conditions include asthma, rheumatoid arthritis, osteoarthritis, bronchitis, chronic obstructive airways disease, psoriasis, allergic rhinitis, atopic dermatitis, shock, and other inflammatory diseases. Hence, these compounds are readily adapted to therapeutic use as selective antagonists of leukotriene D4 for the control and/or treatment of any of the aforesaid clinical conditions in mammals, including humans.

The compounds of the present invention are readily adapted to clinical use as selective antagonists of leukotriene D4. The ability of the compounds or the pharmaceutically acceptable salts thereof to block the leukotriene D4 receptor may be shown by the following in vitro calcium mobilization assay. U-937 cells are grown in 50% RPMI 1640, 50% ethylene glycol dimethyl ether plus 5% heat inactivated FBS, 2 mM 1-glutamine, 100 units/100 μg Pen/Strop and 20 mM 4-(2-hydroxyethyl)-1-piperazine-ethanesulfonic acid (pH=7.4). Two to four days prior to the experiment, U-937 cells are incubated with 1.3% methyl sulfoxide, a treatment which is reported to cause chemotaxis and lysosomal enzyme release in response to chemical mediators (see: Kay et al., *Infect. Immun.*, 41, 1166, (1983)). It appears that U-937 cells are induced to differentiate functionally to a human monocyte-like cell line by the methyl sulfoxide treatment. The cells are seeded at densities of 3–8×10$^5$ cells/ml in 50% RPMI 1640, 50% ethylene glycol dimethyl ether plus 10% heat inactivated FBS, 2 ml glutamine, 100 units/100 μg Pen/Strep, 20 mM 4-(2-hydroxyethyl)-1-piperazine-ethanesulfonic acid (pH=7.4) and 1.35 methyl sulfoxide in spinner culture at 37° C. and grown in a closed system.

Differentiated U-937 cells are harvested on days 2, 3 or 4 by centrifugation at 1000 rpm for 5 minutes. After washing 3 times with a Krebs-Ringer-Hensleit buffer solution, cells (6–12×10$^7$) are resuspended in 15 ml of the buffer (118 mM sodium chloride, 4.6 mM potassium chloride, 1.1 mM magnesium chloride, 1 mM calcium chloride, 5 mM 4-(2-hydroxyethyl)-1-piperazine-ethanesulfonic acid, 24.9 mM sodium hydrogen carbonate, 1 mM potassium hydrogen phosphate, 11.1 mM D-glucose and 0.1% bis(trimethylsilyl) acetamide, pH=7.4). To this cell suspension is added 10 ml of Krebs-Ringer-Hensleit buffer containing 50 μl of fura-2/AM [Molecular Probes Catalog #F-1221, 50 μg/vial, dissolved in 50 μl of silylation grade methyl sulfoxide (Pierce)] prior to an addition to the buffer. The cell mixture is then incubated at 37° C. for 30 minutes. At the end of incubation, 25 ml of warmed Krebs-Ringer-Hensleit buffer (37° C.) is added and the cell suspension is centrifuged at 1000 rpm for 5 minutes. The supernatant is discarded and the cells are resuspended in fresh warm Krebs-ringer-Hensleit buffer. The cell suspension is incubated for an additional 15 minutes at 37° C. to allow for complete hydrolysis of the intracellular fura-2 ester. Twenty-five mls of cold Krebs-Ringer-Hensleit buffer is then added for and the sample is centrifuged at 1000 rpm for 5 minutes. The cells are resuspended at a final concentration of 1×10$^7$ cells/ml in cold Krebs-Ringer-Hensleit buffer and kept at 4° C. until use for fluorescence determination.

The [Ca$^{2+}$]i response is measured by an SLM DMX-100TM spectrofluorometer using an SLM-AMINCO Ion Quantitation Software (Version 3.5). To set up the instrument, 1.8 ml of warmed Krebs-Ringer-Hensleit buffer plus 0.1 ml of fura-2 loaded U-937 cell suspension is placed in a curvette chamber containing a magnetic stir bar. Within the calcium software, the integration is set at 0.9 seconds and the gain on Channel A equal to 100, and adjusted the frequency such that Channel A read approximately 4.5–5.0× 10$^4$ (Channel B automatically changes itself). At the beginning of each experiment, an R$_{max}$ is determined (by addition of 10 μl of 10% Triton X-100 to the curvette which contained 1.8 ml warm Krebs-Ringer-Hensleit buffer plus 0.1 ml fura-2 loaded cells) followed by R$_{min}$ (by addition of 100 mM of ethylenebis(oxyethylenenitrilo)tetraacetic acid to the R$_{max}$ curvette). These values are used by the software to determine [Ca$^{2+}$]i concentration from the ratio of fura-2 emission intensities at two excitation wavelengths (a ratio of 340 nm to 380 nm). After setting the frequency for channel A and then determining R$_{max}$ and R$_{min}$, the machine is ready for acquiring [Ca$^{2+}$]i values. A curvette containing 1.8 ml of warmed Krebs-Ringer-Hensleit buffer and 0.1 ml of cell suspension (2×10$^6$ cells) is placed in the warmed curvette holder. The chamber is then closed and the shutters opened. The software began to acquire a [Ca$^{2+}$]i signal from 0 to 20 seconds. After injection of either drug or methyl sulfoxide vehicle (2 μl) via a special port, the incubation is continued for 180 seconds as the signal is still being recorded. At exact 200 seconds an agonist (dissolved in methylsulfoxide, 2–6 μl) is injected into the curvette through the same port and the signal is recorded for an additional 100 seconds (Total run time=5 minutes). [Ca$^{2+}$]i values are determined by the software (3.5 version).

The ability of the compounds of formula I to compete with radiolabelled LTD4 for specific receptor cites on guinea pig lung membranes may be tested as described by Cheng et al, Biochemical and Biophysical Research Communication, 118, 1, 20–26 (1984).

To evaluate the compounds of the formula I in vivo, they are tested by the aerosolized antigen induced airway obstruction assay procedure.

Male Hartley guinea pigs (300–250 grams) are passively immunized by subcutaneous injection of 0.375 mg/kg of purified guinea pig anti-ovalbumin IgG1, 48–72 hours prior to antigen challenge. Pyrilamino (5 mg/kg) and propranolol (2 mg/kg) are administered subcutaneously 30 minutes prior to challenge. Test compounds are administered into the stomach, either one or two hours prior to challenge, as a suspension in water and 2% Tween-80 using an Argyl feeding tube.

Guinea pigs (5/test dose+5 controls) are then placed in a Tri-R Airborne infection apparatus (model A42). Ovalbumin (OA, 0.01–0.03% yield) is dissolved in 0.9% saline, placed in the glass nobulizer-venturi unit and aerosol generated for 5 minutes (main air flowmeter set at 10). This is followed by a 8 minute cloud decay (vacuum flow set at 7.0).

After removal, animals are killed by injection of approximately 2 ml sodium pentobarbital. Animals die within 1 to 2 minutes of injection. As soon as they die, the animals' pleural spaces are opened by cutting into the xyphoid process allowing the lungs to collapse. Lungs are then removed, the heart cut away, and the trachea tied. The volume of air trapped air in the lugs is determined by measuring the upward force exerted on a 20 gram anchor, when the lungs and anchor are submerged in saline. The volume of trapped gas is normalised to the animals body weight and expressed as excised lung volume (ELGV) in ml/kg.

A test compounds's performance is judged by its ability to reduce the drug treated group mean ELGV below that of the control group mean ELGV. A loglinear regression $$ELGV = \text{slope} \cdot \log(\text{dose}) + \text{intercept}$$

is performed on the grouped mean data and an $ED_{50}$ is calculated as the dose necessary to produce a 50% reduction below the control group ELGV.

$$ELGV50\% = ((\text{control ELGV} - 2)/2) + 2)$$

Data is reported either as the $ED_{50}$ or as the % reduction in control ELGV $$\% \text{ reduction} = (\text{control ELGV} - \text{test drug ELGV})/\text{control ELGV} - 2)$$

at a given test drug dose.

For treatment of the various conditions described above, the compounds of the present invention can be administered to the patient either alone or, preferably, in combination with pharmaceutically acceptable carriers or diluents in a pharmaceutical composition according to standard pharmaceutical practice. Such administration may be carried out in single or multiple doses. A compound can be administered via a variety of conventional routes of administration including orally, the dose range inhalation, and topically. When the compounds are administered orally, the dose range will generally be from about 0.5 to about 50 mg/kg/day for an average adult patient, preferably from about 2 to about 20 mg/kg/day in single or divided doses. If parenteral administration is desired, then an effective dose will generally be from about 0.5 to about 50 mg/kg/day. For intranasal or inhaler administration, the dosage will generally be formulated as a 0.1 to 1% (w/v) solution given in an amount of about 100 to about 1,000 µg/dose given 1 to 4 times daily. The compounds of formula I can also be administered topically in an ointment or cream in concentrations of about 0.5 to about 1%, generally applied 2 or 3 times per day to the affected area. In some instances it may be necessary to use dosages outside these limits, since the dosage will necessarily vary according to the species, age, weight, and response of the individual patient, severity of the patient's symptoms, potency of the particular compound being administered, type of pharmaceutical formulation chosen, and time period and interval at which administration is carried out.

The compounds of the present invention can be administered in a wide variety of different dosage forms, such as in the form of tablets, powders, lozenges, troches, hard candies, sprays, creams, slaves, suppositories, jellies, gels, pastes, lotions, ointments, syrups or capsules, aqueous solutions or suspensions, injectable solutions, elixirs, and the like. Such carriers include solid diluents or fillers, sterile aqueous media and various non-toxic organic solvents, etc. In general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying an/or suspending agents as well, together with such diluents as water, ethanol, propylene glycol, glycerin and various like combinations thereof.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered (preferably pH greater than 8) if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically and this may preferably be done by way of creams, jellies, gels, pastes, ointments and the like, in accordance with standard pharmaceutical practice.

The present invention is illustrated by but is not limited to the specific details of the following Examples and Preparations.

EXAMPLE 1

4-[1-(benzhydryl-carbamoyl)-5-(cyclopentyloxycarbonyl) amino-1H-indol-3-ylmethyl]-3-methoxy-N-o-tolylsulfonylbenzamide (Formula II: $R^3$=H; $R^4$=CH$(C_8H_5)_2$)

To a solution of 4-[5-nitro-1H-indol-3-ylmethyl]-3-methoxy-benzoic acid methylester (0.50 grams, 1.47 mmol) and triethylamine (0.62 mL, 4.41 mmol) in methylene chloride (30 mL), at 0° C., was added a solution of phosgene in toluene (1.9 M in toluene, 1.5 mL, 2.9 mmol). The solution was warmed to room temperature and stirred for 1 hour. To this was added aminodiphenylmethane hydrochloride (0.65 grams, 2.94 mmol) and the resulting solution was stirred for 12 hours at room temperature. The solution was concentrated in vacuo and the crude triturated with methanol. The resulting pale yellow solid was collected via filtration to give 4-[1-(benzhydryl-carbamoyl)-5-nitro-1H-indol-3-ylmethyl]-3-methoxy-benzoic acid methylester (0.672 grams, 83% yield).

To a solution of 4-[1-(benzhydryl-carbamoyl)-5-nitro-1H-indol-3-ylmethyl]-3-methoxy-benzoic acid methylester (0.63 grams, 1.15 mmol) in 1:1 tetrahydrofuran:methanol (30 mL) was added 10% palladium on carbon (0.40 grams). The resulting mixture was hydrogenated at 30 psi for 2.5 hours. The solution was filtered through celite and the filtrate concentrated to give the crude product. Chromatography on silica gel (70% ethyl acetate/hexanes) gave the corresponding amine (0.556 grams, 93% yield).

To a solution of the amine so formed (0.53 grams, 1.02 mmol) and N-methylmorpholine (0.11 mL, 1.02 mmol) in methylene chloride (30 mL) was added cyclopentylchloroformate (0.15 grams, 1.02 mmol). The resulting solution was stirred at room temperature for 15 minutes and then treated with 1 M hydrochloric acid (aq). The mixture was extracted with methylene chloride and the combined organics were dried over magnesium sulfate. Concentration in vacuo gave 4-[1-(benzhydrylcarbamoyl)-5-(cyclopentyloxycarbonyl) amino-1H-indol-3-ylmethyl]-3-methoxy-benzoic acid methylester (0.616 grams, 96% yield).

To a solution of 4-[1-(benzhydryl-carbamoyl)-5-(cyclopentyloxycarbonyl)amino-1H-indol-3-ylmethyl]-3-methoxy-benzoic acid methylester (0.58 grams, 0.92 mmol) in 2:2:1 ratio of tetrahydrofuran:methanol:water (30 mL) was added lithium hydroxide monohydrate (0.19 grams, 4.50 mmol). The resulting solution was stirred at room temperature for 12 hours and then concentrated in vacuo. The crude product was treated with 1 M hydrochloric acid (aq), and the resulting precipitate collected via filtration to give 4-[1-(benzhydryl-carbamoyl)-5-(cyclopentyloxycarbonyl)amino-1H-indol-3-ylmethyl]-3-methoxy-benzoic acid (0.514 grams, 91% yield).

To a solution of 4-[1-(benzhydryl-carbamoyl)-5-(cyclopentyloxycarbonyl)amino-1H-indol-3-ylmethyl]-3-methoxy-benzoic acid (0.50 grams, 0.81 mmol), 4-dimethylaminopyridine (0.015 grams, 1.21 mmol) and 1-[3-(dimethylamino)propyl]-3-ethylcarbodiimide hydrochloride (EDC) (0.23 g, 1.21 mmol) in methylene chloride (30 mL) was added o-tolylsulfonamide (0.14 g, 0.81 mmol). The resulting solution was stirred for 12 hours at room temperature. The solution was diluted with methylene chloride and washed with 1 M hydrochloric acid (aq). The organics were dried over magnesium sulfate and concentrated. Chromatography on silica gel (2% methanol/methylene chloride), followed by recrystallization from wet ether gave the titled compound (0.455 grams, 73% yield). m.p.=253–254° C. Anal. calcd. for $C_{44}H_{42}N_4O_7S$: C, 68.55; H, 5.49; N, 7.27. Found: C, 69.21; H, 5.54; N, 7.14. HRMS calcd. for $C_{44}H_{42}N_4O_7S$: 770.2774. Found 770.2736.

EXAMPLE 2–10

Reaction of the appropriate compound of the formula $NHR^3R^4$ with the requisite 4-[1-(chlorocarbonyl)-5-nitro-1H-indol-3-ylmethyl]-3-methoxy-benzoic acid methylester intermediate, analogous to the procedure of Example 1, affords the following compounds of formula II.

| Ex. # | $R^3$ | $R^4$ | $R^3$ and $R^4$ taken together | M.p.° C. | M.W. |
|---|---|---|---|---|---|
| 2 | hydrogen | benzyl | — | 175 | 694.8 |
| 3 | hydrogen | 2-methoxybenzyl | — | 202 | 724.8 |
| 4 | — | — | 4-chloro-phenyl-phenyl-methyl piperazine | 160 | 910.9 |
| 5 | hydrogen | 1-phenylethyl | — | 172 | 708.8 |
| 6 | hydrogen | phenethyl | — | 130 | 708.8 |
| 7 | hydrogen | 3-phenylpropyl | — | 125 | 722.9 |
| 8 | hydrogen | 2-dimethyl-aminoethyl | — | 182 | 675.8 |
| 9 | hydrogen | 3-pyridyl | — | 277 | 681.8 |
| 10 | methyl | 4-fluorophenyl | — | 140 | 712.8 |

EXAMPLE 11

4-[1-(dimethylcarbamoyl)-5-(cyclopentyloxycarbonylamino-1H-inol-3-ylmethyl]-3-methoxy-N-o-tolylsulfonylbenzamide (Formula III: $R^3$=$CH_3$; $R^4$=$CH_3$; $R^{12}$=cyclopentyl)

To a solution of 4-[5-nitro-1H-indol-3-ylmethyl]-3-methoxy-benzoic acid methylester (0.82 grams, 2.41 mmol) in ethanol (50 mL) was added tin (II) chloride dihydrate (2.70 grams, 12.05 mmol), and the resulting mixture was heated at reflux for 24 hours. The solution was cooled, then concentrated in vacuo. The crude product was treated with 2M sodium hydroxide and extracted with methylene chloride. The combined organics were dried over magnesium sulfate and concentrated. Chromatography on silica gel (40% ethyl acetate/hexanes→2% methanol/methylene chloride) gave the corresponding amine (0.618 grams, 83% yield).

To a solution of the amine so formed (0.618 grams, 2.00 mmol) and N-methylmorpholine (0.22 mL, 2.00 mmol) in methylene chloride (30 mL) was added cyclopentylchloroformate (0.30 grams, 2.0 mmol). The resulting solution was stirred at room temperature for 1 hour. The solution was then diluted with methylene chloride and washed with 1 M hydrochloric acid (aq). The organics were dried over magnesium sulfate and concentrated in vacuo. Chromatography on silica gel (1:1 ethyl acetate:hexanes) gave 4-[5-(cyclopentyloxycarbonyl)amino-1H-indol-3-ylmethyl]-3-methoxy-benzoic acid methylester (0.822 grams, 97% yield).

To a solution of 4-[5-(cyclopentyloxycarbonyl)amino-1H-indol-3-ylmethyl]-3-methoxy-benzoic acid methylester (0.82 grams, 1.95 mmol) in a 2:2:1 ratio of methanol:tetrahydrofuran:water (30 mL) was added lithium hydroxide monohydrate (0.41 grams, 0.73 mmol). The resulting solution was stirred for 12 hours at room temperature. The solution was concentrated, and the crude product treated with 1 hydrochloric acid (aq). The product was collected via filtration. Chromatography on silica gel (1:1 hexanes:ethyl acetate→5% methanol:methylene chloride) gave 4-[5-(cyclopentyloxycarbonyl)amino-1H-indol-3-ylmethyl]-3-methoxy-benzoic acid (0.735 grams, 92 yield).

To a slurry of sodium hydride (60% by wt in mineral oil, 0.037 grams, 0.77 mmol) in dimethylformamide (5 mL), at 0° C., was added a solution of 4-[5-(cyclopentyloxycarbonyl)amino-1H-indol-3-ylmethyl]-3-methoxy-benzoic acid (0.15 grams, 0.37 mmol) in dimethylformamide (5 mL). The resulting solution was stirred at 0° C. for 20 minutes, then dimethylcarbamoyl chloride (0.071 mL, 0.77 mmol) was added. The solution was warmed to room temperature and stirred for 1 hour. The reaction was quenched by addition of 1 M sodium hydroxide (aq), and the mixture was extracted with ethyl acetate. The combined organics were washed with 1 M hydrochloric acid (aq) and set aside. The aqueous phase was made acidic with 1 M hydrochloric acid (aq) and extracted with ethyl acetate. All the organics were combined and dried over magnesium sulfate and concentrated. Chromatography on silica gel (2% methanol/methylene chloride) gave 4-[1-(dimethylcarbamoyl)-5-(cyclopentyloxycarbonyl)amino-1H-indol-3-ylmethyl]-3-methoxy-benzoic acid (0.16 grams, 89% yield).

To a solution of 4-[1-(dimethylcarbamoyl)-5-(cyclopentyloxycarbonyl)amino-1H-indol-3-ylmethyl]-3-methoxy-benzoic acid (0.16 grams, 0.33 mmol), 4-dimethylaminopyridine (0.060 grams, 0.50 mmol) and 1-[3-(dimethylamino)propyl]-3-ethylcarbodiimide hydrochloride (1,2-dichloroethane) (0.096 grams, 0.50 mmol) in methylene chloride (15 mL) was added o-tolylsulfonamide (0.059 grams, 0.34 mmol). The resulting solution was stirred for 12 hours at room temperature. The solution was diluted with methylene chloride and washed with 1 M hydrochloric acid (aq). The organics were dried over magnesium sulfate and concentrated. Chromatography on silica gel (methylene chloride→2% methanol/methylene chloride), followed by recrystallization from wet ether gave the titled compound (0.094 grams, 455 yield). m.p.=152–153° C. HRMS calcd. for $C_{33}H_{36}N_4O_7S$: 632.2348.

EXAMPLES 12–20

Reaction of the appropriate compound of the formula $R^{12}OCOCl$ with the requisite 4-[5-amino-1H-indol-3-ylmethyl]-3-methoxy-benzoic acid ethylester intermediate and the reaction of the appropriate compound of the formula $R^3R^4NCOCl$ with the requisite 4-[5-(cyclopentyloxycarbonyl)amino-1H-indol-3-ylmethyl]-3-methoxybenzoic acid intermediate, analogous to the procedure of Example 11, affords the compounds of formula III.

| Ex. # | $R^3$ | $R^4$ | $R^3$ and $R^4$ taken together | $R^{12}$ | M.P. ° C. | M.W. |
|---|---|---|---|---|---|---|
| 12 | ethyl | ethyl | — | cyclopentyl | 138 | 660.8 |
| 13 | — | — | morpholinyl | cyclopentyl | 146 | 674.8 |
| 14 | methyl | phenyl | — | cyclopentyl | 138 | 694.8 |
| 15 | phenyl | phenyl | — | cyclopentyl | 150 | 756.9 |
| 16 | — | — | pyrrolidinyl | cyclopentyl | 190 | 658.8 |
| 17 | ethyl | ethyl | — | endo-bicyclo-[2.2.1]-heptanyl | 195 | 686.8 |
| 18 | phenyl | phenyl | — | endo-bicyclo-[2.2.1]-heptanyl | 206 | 782.9 |
| 19 | phenyl | phenyl | — | exo-bicyclo-[2.2.1]-heptanyl | 239 | 782.9 |
| 20 | ethyl | ethyl | — | exo-bicyclo-[2.2.1]-heptanyl | 223 | 686.8 |

EXAMPLE 21

4-[1-(4-fluoro-phenylcarbamoyl)-5-(cyclopentyloxycarbonyl)amino-1H-indol-3-ylmethyl]-3-methoxy-N-o-tolylsulfonylbenzamide (Formula II: $R^3$=4-fluorophenyl; $R^4$=hydrogen)

To a stirred solution of 4-[5-nitro-1H-indol-3-ylmethyl]-3-methoxy-benzoic acid methylester (1.30 grams, 3.82 mmol) and 4-dimethylaminopyridine (0.58 mL, 4.77 mmol) in methylene chloride (60 mL) was added 4-fluorophenylisocyanate (0.70 mL, 5.73 mmol). The resulting solution was stirred for 18 hours, at room temperature, and then diluted with methylene chloride. The solution was washed with 1 M hydrochloric acid, water and brine, then dried over magnesium sulfate. Concentration in vacuo followed by trituration in diethylether gave 4-[1-(4-fluorophenylcarbamoyl)-5-nitro-1H-indol-3-ylmethyl]-3-methoxy-benzoic acid methylester (1.60 grams, 88% yield).

To a solution of 4-[1-(4-fluoro-phenylcarbamoyl)-5-nitro-1H-indol-3-ylmethyl]-3-methoxy-benzoic acid methylester (1.50 grams, 3.14 mmol) in a 1:1 ratio of tetrahydrofuran:ethyl acetate (200 mL) was added 10% palladium on carbon (1.50 grams) and the resulting mixture was hydrogenated at 30 psi at room temperature for 1 hour. The mixture was filtered through celite and the filtrate concentrated in vacuo to give the crude product. Trituration in ethyl acetate/hexanes gave the corresponding amine (1.20 grams, 86% yield).

To a solution of the amine so formed (1.17 grams, 2.61 mmol) and N-methylmorpholine (0.60 mL, 5.23 mmol) in methylene chloride (10 mL) was added cyclopentylchloroformate (0.39 grams, 2.61 mmol). The solution was stirred at room temperature for 18 hours, then diluted with ethyl acetate. The resulting solution was washed with 1 M hydrochloric acid (aq), 5% sodium hydrogen carbonate (aq), water, and brine, then dried over magnesium sulfate. Concentration in vacuo, followed by recrystallization from ethyl acetate/hexanes gave 4-[1-(4-fluoro-phenylcarbamoyl)-5-(cyclopentyloxycarbonyl)amino-1H-indol-3-ylmethyl]-3-methoxy-benzoic acid methylester (1.35 grams, 92% yield).

To a solution of 4-[1-(4-fluoro-phenylcarbamoyl)-5-(cyclopentyloxycarbonyl)amino-1H-indol-3-ylmethyl]-3-methoxy-benzoic acid methylester (1.30 grams, 2.32 mmol) in a 1:1:1 ratio of tetrahydrofuran:methanol:water (30 mL) was added lithium hydroxide monohydrate (0.20, 4.64 mmol) and the resulting solution was stirred, at room temperature, for 22 hours. The reaction mixture was made acidic with 1 M hydrochloric acid (aq) and extracted with chloroform. The combined organics were washed with water and brine then dried over magnesium sulfate. Concentration in vacuo gave 4-[1-(4-fluoro-phenylcarbamoyl)-5-(cyclopentyloxycarbonyl)-amino-1H-indol-3-ylmethyl]-3-methoxy-benzoic acid (1.20 grams, 95% yield).

To a stirred suspension of 4-[1-(4-fluoro-phenylcarbamoyl)-5-(cyclopentyloxycarbonyl)-amino-1H-indol-3-ylmethyl]-3-methoxy-benzoic acid (1.28 grams, 2.35 mmol), o-tolylsulfonamide (0.44 grams, 2.58 mmol), and 4-dimethylaminopyridine (0.34 grams, 2.82 mmol) in methylene chloride (40 mL) was added 1-[3-(dimethylamino)propyl]-3-ethylcarbodiimide hydrochloride (0.54 grams, 2.82 mmol). The mixture was stirred at room temperature for 18 hours, then diluted with methylene chloride. The solution was washed with 1 M hydrochloric acid (aq), water and brine then dried over magnesium sulfate. Concentration in vacuo, followed by chromatography on silica gel (1:19 methanol:methylene chloride) gave 1.3 grams of the titled compound as a foam. Further purification by triturating in methylene chloride gave the titled compound (0.810 grams, 49% yield). m.p.=230° C. (decomp.). Anal. calcd. for $C_{37}H_{35}N_4SO_7F$·2 water: C, 60.48, H, 5.35; N, 7.62. Found: C, 59.75; H, 5.22; N, 7.57.

EXAMPLES 22–26

Reaction of the appropriate compound of the formula $R^3NCO$ with the requisite 4-[5-nitro-1H-indol-3-ylmethyl]-3-methoxy-benzoic acid methylester intermediate, analogous to the procedure of Example 21, affords the following compounds of formula II, wherein $R^4$ is hydrogen.

| Example # | $R^3$ | M.P.° C. | M.W. |
| --- | --- | --- | --- |
| 22 | methyl | 182 | 618.7 |
| 23 | tert-butyl | 160 | 660.9 |
| 24 | 2,4-difluorophenyl | 190 | 716.8 |
| 25 | 2-chlorophenyl | — | 715.1 |
| 26 | phenyl | — | 680.8 |

EXAMPLE 27

4-[1-(carbomoyl)-5-(cyclopentyloxycarbonyl)amino-1H-indol-3-ylmethyl]-3-methoxy-N-o-tolylsulfonylbenzamide To a solution of 4-[5-nitro-1H-indol-3-ylmethyl]-3-methoxy-benzoic acid methylester (5.04 grams, 14.80 mmol) in methylene chloride (150 mL) was added chlorosulfonylisocyanate (1.3 mL, 14.80 mmol) and the resulting solution was stirred for 5 days at room temperature. The solution was then concentrated in vacuo, and the crude product dissolved in a 6:1 ratio of acetone:water (180 mL). The pH of this solution was adjusted to approx. 8 by the addition of 2 M sodium hydroxide (aq). The resulting mixture was stirred, at room temperature, for 45 minutes. The reaction was diluted with water (300 mL) and the resulting suspension was stirred for 30 minutes. Filtration, followed by trituration of the solid in methanol gave 4-[1-carbamoyl-5-nitro-1H-indol-3-ylmethyl]-3-methoxy-benzoic acid methylester (1.75 grams). The filtrate was concentrated, and the crude chromatographed on silica gel (2.5% methanol/methylene chloride) to give additional 4-[1-carbamoyl-5-nitro-1H-indol-3-ylmethyl]-3-methoxy-benzoic acid methylester (0.36 grams, 37% yield overall).

To a solution of 4-[1-carbamoyl-5-nitro-1H-indol-3-ylmethyl]-3-methoxy-benzoic acid methylester (1.99 grams, 5.19 mmol) in a 4:1 ratio of tetrahydrofuran:ethyl acetate (250 mL) was added 10% palladium on carbon (1.5 grams) and the resulting mixture was hydrogenated at 35 psi, at room temperature, for 3.5 hours. The mixture was filtered through celite, and the filtrate concentrated in vacuo. Recrystallization form a 4:1 ratio of methylene chloride:methanol gave the corresponding amine (0.727 grams). The mother liquor was concentrated and the crude chromatographed on silica gel (5% methanol/methylene chloride) to give additional amine (0.446 grams, 64% overall).

To a solution of the amine so formed (1.16 grams, 3.28 mmol) and N-methylmorpholine (0.072 mL, 6.56 mmol) in methylene chloride (40 mL) was added cyclopentylchloroformate (0.68 grams, 4.59 mmol). The resulting solution was stirred, at room temperature, for 3 days, then diluted with methylene chloride. The resulting solution was washed with 1 M hydrochloric acid (aq), water, and brine, then dried over sodium sulfate. The combined aqueous washings contained a suspension, which upon filtration gave 4-[1-carbamoyl-5-(cyclopentyloxycarbonyl)amino-1H-indol-3-ylmethyl]-3-methoxy-benzoic acid methylester (1.05 grams). The organic phase was concentrated in vacuo, followed by chromatography on silica gel (25% ethyl acetate/methylene chloride) to give additional 4-[1-carbamoyl-5-(cyclopentyloxycarbonyl)amino-1H-indol-3-ylmethyl]-3-methoxy-benzoic acid methylester (0.118 grams, 76% yield overall).

To a solution of 4-[1-carbamoyl-5-(cyclopentyloxycarbonyl)amino-1H-indol-3-ylmethyl]-3-methoxy-benzoic acid methylester (1.15 grams, 2.47 mmol) in a 6:1 ratio tetrahydrofuran:water (70 mL) was added lithium hydroxide monohydrate (0.21 grams, 4.94 mmol) and the resulting solution was stirred, at room temperature, for 46 hours. The reaction mixture was concentrated in vacuo to a volume of 15 mL, then diluted with water (300 mL). The aqueous solution was acidified by addition of 1 M hydrochloric acid (aq), and the resulting precipitate was collected via filtration to give 4-[1-carbamoyl-5-(cyclopentyloxycarbonyl)amino-1H-indol-3-ylmethyl]-3-methoxy-benzoic acid (1.04 grams, 93% yield).

To a suspension of 4-[1-carbamoyl-5-(cyclopentyloxycarbonyl)amino-1H-indol-3-ylmethyl]-3-methoxy-benzoic acid (1.03 grams, 2.28 mmol), o-tolylsulfonamide (0.39 grams, 2.28 mmol) and 4-dimethylaminopyridine (0.42 grams, 3.42 mmol) in methylene chloride (50 mL) was added 1-[3-(dimethylamino)propyl]-3-ethylcarbodiimide hydrochloride (0.66 grams, 3.42 mmol). The reaction was stirred for 4 days at room temperature, then diluted with methylene chloride (700 mL). This solution was washed with 1 M hydrochloric acid (aq), water, and brine, then dried over sodium sulfate. Concentration in vacuo, followed by chromatography on silica gel (10% methanol/methylene chloride) gave the titled compound (0.90 grams, 65% yield). HRMS calcd. for $C_{31}H_{32}N_4O_7Na$: 627.1904. Found: 611.1924.

EXAMPLE 28

4-(1-difluoromethyl-5-(cyclopentyloxycarbonyl)amino-1H-indol-3-ylmethyl-3-methoxy-N-o-tolylsulfonylbenzamide To a solution of 4-[5-nitro-1H-indol-3-ylmethyl]-3-methoxy-benzoic acid methylester (0.15 grams, 0.44 mmol) in dimethylformamide (5 mL) was added sodium hydride (60% by wt. in mineral oil, 0.019 grams, 0.48 mmol). After stirring 20 minutes, at room temperature, freon was bubbled into the reaction mixture for approximately 5 minutes. The reaction was accompanied by a color change from deep-red/brown to a light green/yellow. The reaction was quenched by addition of water, and the solution was extracted with ethyl acetate. The combined organics were washed with water and brine, then dried over sodium sulfate. Concentration in vacuo, followed by chromatography on silica gel (methylene chloride) gave 4-[1-difluoromethyl-5-nitro-1H-indol-3-ylmethyl]-3-methoxy-benzoic acid methylester (0.128 grams, 75% yield).

To a solution of 4-[1-difluoromethyl-5-nitro-1H-indol-3-ylmethyl]-3-methoxybenzoic acid methylester (0.39 grams, 1.00 mmol) in tetrahydrofuran (50 mL) was added 10% palladium on carbon (0.20 grams). The resulting solution was hydrogenated at 40 psi at room temperature for 4 hours. The mixture was filtered through celite and washed with tetrahydrofuran. The filtrate was concentrated in vacuo to give the crude product as a foam. Chromatography on silica gel (5% methanol/methylene chloride) gave the corresponding amine (0.15 grams, 42% yield).

To a solution of the amine so formed (0.15 grams, 0.42 mmol) and N-methylmorpholine (0.14 mL, 1.26 mmol) in methylene chloride (8 mL), at 0° C., was added cyclopentylchloroformate (0.058 mL, 0.47 mmol). The resulting solution was warmed to room temperature and stirred for 12 hours. The reaction mixture was treated with water and extracted with methylene chloride. The combined organics were washed with 1 M hydrochloric acid (aq) and brine then dried over sodium sulfate. Concentration in vacuo, followed by chromatography (10% ethyl acetate/methylene chloride) gave 4-[1-difluoromethyl-5-(cyclopentyloxycarbonyl) amino-1H-indol-3-ylmethyl]-3-methoxy-benzoic acid methylester (0.185 grams, 95% yield).

To a solution of 4-[1-difluoromethyl-5-(cyclopentyloxycarbonyl)amino-1H-indol-3-ylmethyl]-3-methoxy-benzoic acid methylester (0.40 grams, 0.84 mmol) in a 5:5:2 ratio of methanol tetrahydrofuran:water (24 mL) was added lithium hydroxide monohydrate (0.18 grams, 4.18 mmol). The resulting solution was stirred for 24 hours at room temperature. The reaction mixture was then acidified with 1 M hydrochloric acid (aq) and extracted with ethyl acetate. The combined organics were washed with water and brine, then dried over sodium sulfate. Concentration in vacuo gave 4-[1-difluoromethyl-5-(cyclopentyloxycarbonyl)amino-1H-indol-3-ylmethyl]-3-methoxy-benzoic acid as a white solid (0.40 grams, 100% yield). An analytical sample was attained by recrystallization from ethyl acetate/hexanes.

To a solution of 4-[1-difluoromethyl-5-(cyclopentyloxycarbonyl)amino-1H-indol-3-ylmethyl]-3-methoxy-benzoic acid (1.10 grams, 2.37 mmol), 4-dimethylaminopyridine (0.44 grams, 3.63 mmol) and 1-[3-dimethylamino)propyl]-3-ethylcarbodiimide hydrochloride (1,2-dichloroethane) (0.70 grams, 3.64 mmol) in methylene chloride (100 mL) was added o-tolylsulfonamide (0.41 grams, 2.42 mmol). The resulting solution was stirred for 16 hours at room temperature. The solution was diluted with methylene chloride and washed with 1 M hydrochloric acid (ag) and brine. The organics were dried over sodium sulfate and concentrated. Chromatography on silica gel (5% methanol/methylene chloride gave 4-[1-difluoromethyl-5-(cyclopentyloxycarbonyl)amino-1H-indol-3-ylmethyl]-3-methoxy-N-o-tolylsulfonylbenzamide (1.10 grams, 76% yield). HRMS calcd. for $C_{31}H_{31}N_3O_6F_2S$: 611.1902. Found: 611.1924.

EXAMPLE 29

4-[1-formyl-5-(cyclopentyloxycarbonyl)amino-1H-indol-3-ylmethyl]-3-methoxy-N-o-tolylsulfonylbenzamide To a solution of 4-[1-difluoromethyl-5-(cyclopentyloxycarbonyl)amino-1H-indol-3-ylmethyl]-3-methoxy-N-o-tolylsulfonylbenzamide (0.10 grams, 0.16 mmol) in chloroform (5 mL) was added a solution of hydrochloric acid (1 M in ether, 0.16 mL, 0.16 mmol). The resulting solution was stirred for 4 hours, at room temperature, then concentrated in vacuo. Chromatography on silica gel (5% methanol, methylene chloride) gave the titled compound (0.92 grams, 96% yield). m.p.=145° C. (decomp.) HRMS calcd. for $C_{31}H_{31}N_3O_7$: 590.1961. Found: 590.1914.

EXAMPLE 30

4-[1-diethylcarbamoyl-5-(4,4,4-trifluoro-2-methyl-butylcarbamoyl)-1H-indol-3-ylmethyl]-3-methoxy-N-o-tolylsulfonylbenzamide (Formula V: $R^3=C_2H_5$; $R^4=C_2H_5$)

To a solution of 4-[5-benzoxycarbonyl-1H-indol-3-ylmethyl]-3-methoxy-benzoic acid methylester (3.46 grams, 8.06 mmol) in dimethylformamide (40 mL) and formic acid (2 mL) was added 10% palladium on carbon (1.5 grams). The resulting mixture was hydrogenated at 30 psi for 1.5 hours. The mixture was filtered through celite and the filtrate diluted with ethyl acetate. This solution was washed several times with 1 M hydrochloric acid (aq). The organics were then dried over magnesium sulfate and concentrated. Recrystallization from methylene chloride gave 3-(2-methoxy-4-methoxycarbonyl-benzyl)-1H-indole-5-carboxylic acid (1.97 grams, 73% yield).

To a solution of 3-(2-methoxy-4-methoxycarbonyl-benzyl)-1H-indole-5-carboxylic acid (1.7 grams, 5.00 mmol) in methylene chloride (50 mL), was added 4-dimethylaminopyridine (0.67 grams, 5.50 mmol), 1,2-dichloroethane (1.06 grams, 5.50 mmol), triethylamine (0.73 mL, 5.25 mmol) and 4,4,4-trifluoro-2-methylbutylamine hydrochloride (0.93 grams, 5.25 mmol). The resulting solution was stirred 12 hours, at room temperature, then diluted with methylene chloride. The solution was washed with 1 M hydrochloric acid (aq), then the organics were dried over magnesium sulfate. Concentration in vacuo followed by trituration of the crude product in a 2:1 ratio of ether:hexanes gave 3-methoxy-4-[5-(4,4,4-trifluoro-2-methyl-butylcarbamoyl)-1H-indol-3-ylmethyl]-benzoic acid methylester (1.88 grams, 82% yield).

To a solution of 3-methoxy-4-[5-(4,4,4-trifluoro-2-methyl-butylcarbamoyl)-1H-indol-3-ylmethyl]-benzoic acid methylester (1.80 grams, 3.90 mmol) in 2:2:1 methanol:tetrahydrofuran:water (30 mL) was added lithium hydroxide monohydrate (0.82 grams, 19.50 mmol). The resulting solution was stirred, at room temperature, for 48 hours then concentrated in vacuo. The resulting crude product was treated with 1 M hydrochloric acid (aq), and the resulting precipitate was collected via filtration to vie 3-methoxy-4-[5-(4,4,4-trifluoro-2-methyl-butylcarbamoyl)-1H-indol-3-ylmethyl]-benzoic acid (1.74 grams, 99% yield).

To a solution of 3-methoxy-4-[5-(4,4,4-trifluoro-2-methyl-butylcarbamoyl)-1H-indol-3-ylmethyl]-benzoic acid (1.54 grams, 3.43 mmol), triphenylphosphine (1.26 grams, 4.8 mmol) and benzyl alcohol (0.50 mL, 4.8 mmol) in tetrahydrofuran (50 mL), at 0° C., was added diethyl azodicarboxylate (0.65 mL, 4.1 mmol). The reaction is then warmed to room temperature and stirred 12 hours. Concentration in vacuo followed by chromatography on silica gel (1:1 hexanes:ethyl acetate) gave 3-methoxy-4-[5-(4,4,4-trifluoro-2-methyl-butylcarbamoyl)-1H-indol-3-ylmethyl]-benzoic acid benzylester with impurities present. The product was dissolved in cold ether, and filtered. The filtrate was concentrated, and the remaining yellow foam was chromatographed on silica gel (1:1 cyclohexane:ethyl acetate) to give 3-methoxy-4-[5-(4,4,4-trifluoro-2-methyl-butylcarbamoyl)-1H-indol-3-ylmethyl]-benzoic acid benzylester (1.56 grams, 87% yield).

To a slurry of sodium hydride (60% by wt. in mineral oil, 0.035 grams, 0.72 mmol) in dimethylformamide (3 mL), at 0° C., was added 3-methoxy-4-[5-(4,4,4-trifluoro-2-methyl-butylcarbamoyl)-1H-indol-3-ylmethyl]-benzoic acid benzylester (0.35 grams, 0.65 mmol). The resulting solution was stirred for 15 minutes, at 0° C., then diethylcarbamoyl chloride (0.082 mL, 0.65 mmol) was added. The solution was warmed to room temperature and stirred for 12 hours. The solution was diluted with ethyl acetate and washed with 1 M hydrochloric acid (aq). The organics were dried over magnesium sulfate and concentrated in vacuo. Chromatography on silica gel (30% ethyl acetate/hexanes) gave the 1-indole-diethylamide analog (0.316 grams, 76% yield).

To a solution of the ureido compound (0.30 grams, 0.47 mmol) in ethyl acetate (30 mL) was added 10% palladium on carbon (0.20 grams). The mixture was hydrogenated at 30 psi for 2 hours, then filtered through celite and concentrated in vacuo. Chromatography on silica gel (ether→5% methanol/methylene chloride) gave 4-[1-diethylcarbamoyl-5-(4,4,4-trifluoro-2-methyl-butylcarbamoyl)-1H-indol-3ylmethyl]-3-methoxy-benzoic acid (0.197 grams, 76% yield).

To a solution of 4-[1-diethylcarbamoyl-5-(4,4,4-trifluoro-2-methylbutylcarbamoyl)-1H-indol-3-ylmethyl]-3-methoxy-benzoic acid (0.12 grams, 0.22 mmol), 4-dimethylaminopyridine (0.040 grams, 0.33 mmol) and 1,2-dichloroethane (0.063 grams, 0.33 mmol) in methylene chloride (15 mL) was added o-tolylsulfonamide (0.038 grams, 0.22 mmol). The resulting solution was stirred, at room temperature, for 12 hours. The reaction mixture was then diluted with methylene chloride and washed with 1 M hydrochloric acid (aq). The organics were dried over magnesium sulfate and concentrated in vacuo. Recrystallization from wet ether gave the titled compound (0.115 grams, 75% yield), m.p.=153–154° C. Anal calcd. for $C_{35}H_{39}N_4O_6SF_3$: C, 59.92; H, 5.60; N, 7.99. Found: C, 60.18; H, 5.68; N, 8.41.

EXAMPLES 31–32

Reaction of the appropriate compound of formula $R^3R^4NCOCl$ with the requisite 4-[5-(4,4,4-trifluoro-2-methyl-butylcarbamoyl)-1H-indol-3-ylmethyl benzoic acid intermediate, analogous to the procedure of Example 29, affords the compound of formula V.

| Example # | $R^3$ | $R^4$ | M.P.° C. | M.W. |
|---|---|---|---|---|
| 31 | methyl | phenyl | 157 | 734.8 |
| 32 | phenyl | phenyl | 168 | 796.9 |

We claim:

1. A compound of the formula

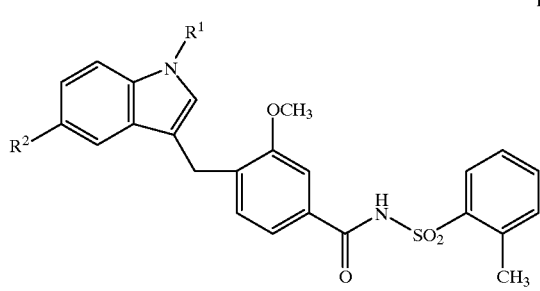

I or a pharmaceutically acceptable salt thereof, wherein $R^1$ is CHO, $CH_2F$, $CHF_2$ or $CONR^3R^4$ wherein $R^3$ and $R^4$ are each independently selected from the group consisting of hydrogen, ($C_1$–$C_6$alkyl, ($C_2$–$C_6$)alkenyl, ($C_2$–$C_6$)alkynyl, ($C_6$–$C_{10}$)aryl, ($C_6$–$C_{10}$)aryl ($C_1$–$C_6$) alkyl, (($C_1$–$C_6$)alkyl)$_3$amino ($C_1$–$C_6$)alkyl, pyridinyl and $CHR^5R^6$ wherein $R^5$ and $R^6$ are each independently ($C_1$–$C_6$)alkyl or ($C_6$–$C_{10}$) aryl;

or $R^3$ and $R^4$ together with the nitrogen to which they are attached form morpholinyl, pyrrolidinyl or a group of the formula

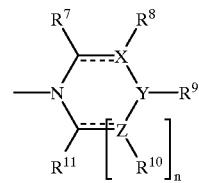

wherein the broken lines represent optional double bonds;

n is 0, 1 or 2;

X, Y and Z are each independently CH, O, S or N; and $R^7R^8$, $R^9$, $R^{10}$ and $R^{11}$ are each independently selected from the group consisting or hydrogen, ($C_1$–$C_6$)alkyl, ($C_2$–$C_6$)alkenyl, ($C_2$–$C_6$)alkynyl, ($C_6$–$C_{10}$)aryl, ($C_6$–$C_{10}$)aryl ($C_1$–$C_6$)alkyl, (($C_1$–$C_6$)alkyl)$_2$amino ($C_1$–$C_6$)alkyl, pyridinyl, $CHR^5R^6$ wherein $R^5$ and $R^6$ are each independently ($C_1$–$C_6$)alkyl or ($C_6$–$C_{10}$)aryl; or benzhydryl optionally substituted by one to five halo;

or $R^7$ and $R^8$, $R^8$ and $R^9$, $R^9$ and $R^{10}$, or $R^{10}$ and $R^{11}$ together form a benzo group;

$R^2$ is a group of the formula

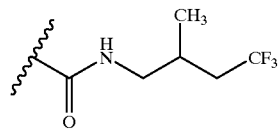

or a group of the formula

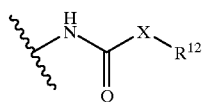

wherein X is O, NH or $CH_2$; and
$R^{12}$ is $(C_3-C_7)$cycloalkyl or a group of the formula

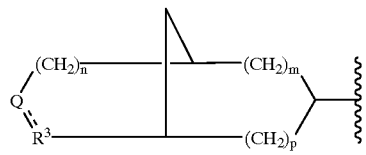

wherein the broken line represents an optional double bond; n is 0 or 1; m is 0, 1 or 2; p is 0, 1 or 2; Q and $R^3$ are both CH or both $CH_2$;

with the proviso that when Q and $R^3$ are both CH, the broken line represents a double bond; and with the proviso that when n is 1 or 2, only two of the three variables X, Y and Z can be O, S or N.

2. A compound according to claim 1, wherein $R^1$ is $CONR^3R^4$ wherein $R^3$ and $R^4$ are each independently selected from $(C_1-C_6)$alkyl, $(C_8-C_{10})$aryl and $(C_8-C_{10})$aryl $(C_1-C_8)$alkyl.

3. A compound according to claim 1, wherein X is O and $R^{12}$ is cyclopentyl.

4. A compound according to claim 1, wherein $R^1$ is $CONR^3R^4$ wherein $R^3$ and $R^4$ are each independently selected from $(C_1-C_6)$alkyl, $(C_8-C_{10})$aryl and $(C_6-C_{10})$aryl $(C_1-C_6)$alkyl; X is $CH_2$ and $R^{12}$ is cyclopentyl.

5. A compound according to claim 1, wherein said compound is selected from the group consisting of:

4-[1-formyl-5-(cyclopentyloxycarbonyl)amino-1H-indol-3-ylmethyl]-3-methoxy-N-o-tolylsulfonylbenzamide;

4-[1-(hydroxycarbamoyl)-5-(cyclopentyloxycarbonyl) amino-1H-indol-3-ylmethyl]-3-methoxy-N-o-tolylsulfonylbenzamide;

4-[1-((2-carboxyethyl)carbamoyl)-5-(cyclopentyloxycarbonyl)amino-1H-indol-3-ylmethyl]-3-methoxy-N-o-tolylsulfonylbenzamide;

4-[1-((2-tetrazolylethyl)carbamoyl)-5-(cyclopentyloxycarbonyl)amino-1H-indol-3-ylmethyl]-3-methoxy-N-o-tolylsulfonylbenzamide;

4-[1-(methylphenylcarbamoyl)-5-(cyclopentyloxycarbonyl)amino-1H-indol-3-ylmethyl]-3-methoxy-N-o-tolylsulfonylbenzamide;

4-[1-(diphenylcarbamoyl)-5-(cyclopentyloxycarbonyl) amino-1H-indol-3-ylmethyl]-3-methoxy-N-o-tolylsulfonylbenzamide;

4-[1-carbamoyl-5-(cyclopentyloxycarbonyl)amino-1H-indol-3-ylmethyl]-3-methoxy-N-o-tolylsulfonylbenzamide; and 4-[1-(pyrrolidine-carbonyl)-5-(cyclopentyloxycarbonyl) amino-1H-indol-3-ylmethyl]-3-methoxy-N-o-tolylsulfonylbenzamide.

6. A pharmaceutical composition for (a) treating a condition selected form the group consisting of asthma, rheumatoid arthritis, osteoarthritis, bronchitis, chronic obstructive airways diseases, psoriasis, allergic rhinitis, atopic dermatitis, and shock or (b) blocking the leucotriene D4 receptor in a mammal comprising a leucotriene D4 receptor blocking amount of a compound of claim 1, and a pharmaceutically acceptable carrier.

7. A method of (a) treating a condition selected from the group consisting of asthma, rheumatoid arthritis, osteoarthritis, bronchitis, chronic obstructive airways diseases, psoriasis, allergic rhinitis, atopic dermatitis, and shock or blocking the leucotriene D4 receptor in a mammal comprising administering to said mammal an amount of a compound of claim 1, effective in treating such a condition.

8. A method of blocking the leukotriene D4 receptor in a mammal, comprising administering to said mammal a leukotriene D4 receptor blocking amount of a compound of claim 1.

9. The pharmaceutical composition of claim 6, wherein said mammal is a human.

10. The method of claim 7, wherein said mammal is a human.

11. The method of claim 8, wherein said mammal is a human.

* * * * *